US011958795B2

(12) United States Patent
Palasch

(10) Patent No.: US 11,958,795 B2
(45) Date of Patent: Apr. 16, 2024

(54) CHLORIDE SALT ELIMINATOR FOR GLYCOL IN NATURAL GAS DEHYDRATION

(71) Applicant: GLY-TECH SERVICES, INC., Harvey, LA (US)

(72) Inventor: Michael J. Palasch, New Orleans, LA (US)

(73) Assignee: GLY-TECH SERVICES, INC., Harvey, LA (US)

(*) Notice: Subject to any disclaimer, the term of this patent is extended or adjusted under 35 U.S.C. 154(b) by 52 days.

(21) Appl. No.: 17/690,384

(22) Filed: Mar. 9, 2022

(65) Prior Publication Data
US 2023/0286891 A1    Sep. 14, 2023

(51) Int. Cl.
C07C 29/76     (2006.01)
B01D 39/20     (2006.01)
C07C 37/68     (2006.01)
C07C 37/70     (2006.01)
C10L 3/10      (2006.01)

(52) U.S. Cl.
CPC ........ C07C 37/685 (2013.01); B01D 39/2003 (2013.01); B01D 39/2027 (2013.01); C07C 29/76 (2013.01); C07C 37/70 (2013.01); C10L 3/106 (2013.01); C10L 2290/08 (2013.01)

(58) Field of Classification Search
CPC .............................. C07C 29/74–94
See application file for complete search history.

(56) References Cited

U.S. PATENT DOCUMENTS

| | | | |
|---|---|---|---|
| 4,026,681 A * | 5/1977 | Roskelley | B01D 53/263 95/194 |
| 4,518,396 A | 5/1985 | Rawson | |
| 5,817,889 A | 10/1998 | Pondebat et al. | |
| 5,882,486 A | 3/1999 | Moore, Jr. | |
| 6,023,003 A | 2/2000 | Dunning et al. | |
| 6,251,166 B1 | 6/2001 | Anderson | |
| 7,232,505 B2 | 6/2007 | Laborie et al. | |
| 7,267,775 B2 | 9/2007 | Baudot et al. | |
| 8,876,954 B2 | 11/2014 | Witherspoon et al. | |
| 2010/0281775 A1 | 11/2010 | Logue | |

* cited by examiner

*Primary Examiner* — Medhanit W Bahta
(74) *Attorney, Agent, or Firm* — KEATY LAW FIRM LLC; Thomas S. Keaty

(57) ABSTRACT

A chloride salt eliminator system and method for removal of chloride salt from glycol circulated through a reboiler in natural gas dehydration, in a continuous process, close to the wellhead. Hot glycol from the reboiler is pumped into a salt eliminator unit having independently replaceable filter elements which trap chloride salts which are not soluble in hot glycol and pass clean glycol for return to the reboiler.

1 Claim, 1 Drawing Sheet

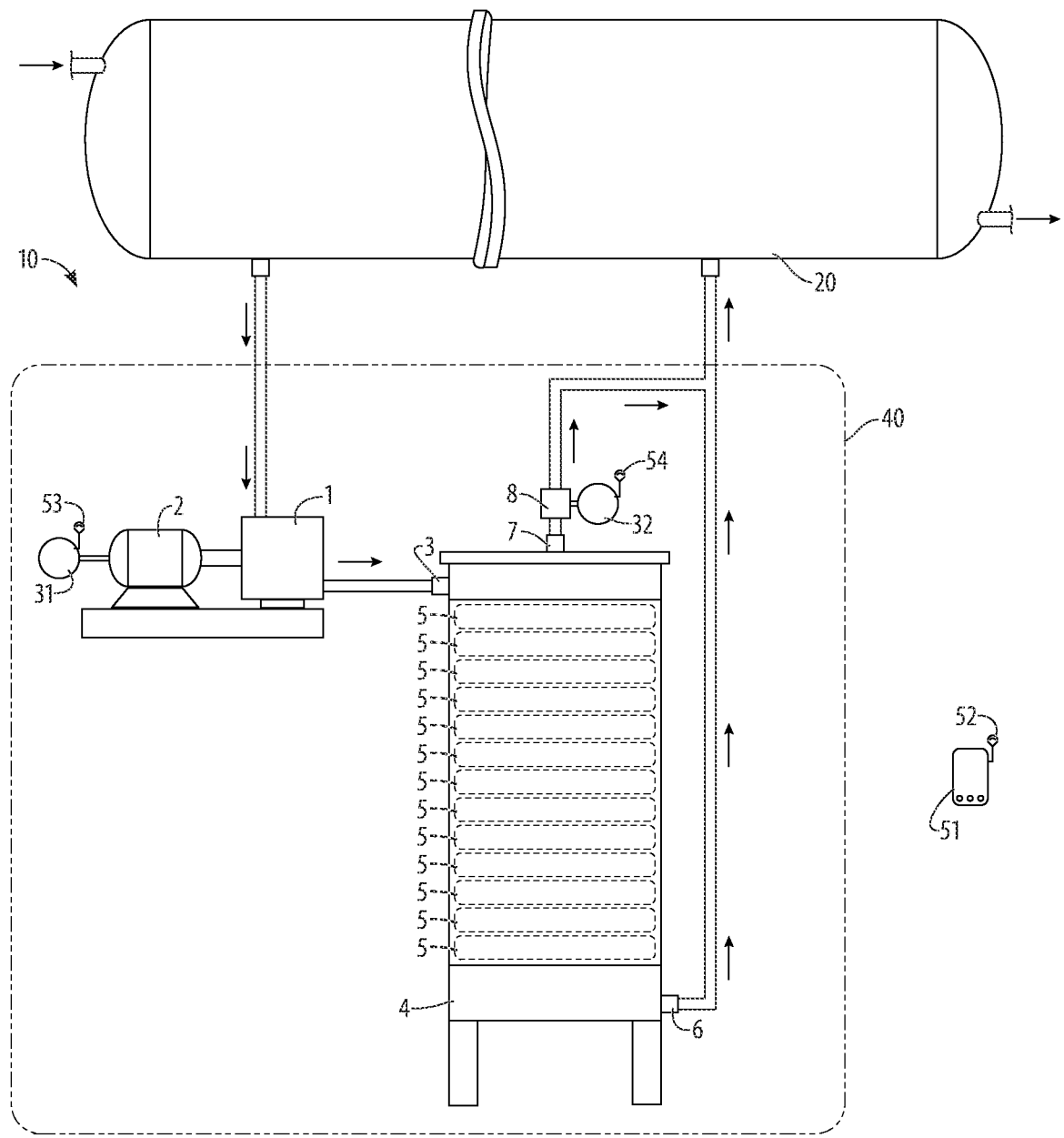

CHLORIDE SALT ELIMINATOR FOR GLYCOL IN NATURAL GAS DEHYDRATION

BACKGROUND OF THE INVENTION

This invention provides a chloride salt eliminator system and method for removal of chloride salt from glycol circulated through a reboiler in natural gas dehydration.

The overall process of natural gas dehydration, within which the instant invention provides novel improvements, is described in detail in application Ser. No. 12/387,984, "System for Dehydrating Natural Gas," filed May 11, 2009, now abandoned, the full disclosure of which is incorporated by reference herein as additional detailed disclosure of the overall system and method of dehydration of natural gas which this new invention improves upon.

Natural gas at the wellhead comprises methane mixed with several extraneous materials, including hazardous materials, with other hydrocarbons, and with water or water vapor and with chloride salts such as sodium chloride (NaCl) and calcium chloride (CaCL2). Before such natural gas at the wellhead can be introduced into a pipeline and sold as natural gas to customers, most of the extraneous materials must be removed. Relevant here, the water or water vapor, along with the chloride salts dissolved in the water, must be removed close to the wellhead to avoid clogging and corroding pipelines. Glycol, especially triethylene glycol (TEG) is used to remove water and dissolved chloride salts through contact with the "wet" natural gas, usually in a contact tower at or near the wellhead. Fresh glycol is in a "lean" or "clean" state, with a great affinity for absorbing water and other extraneous materials. The glycol becomes laden with extraneous materials absorbed from the "wet" natural gas, becoming "wetted" or "rich," and therefore becomes less able to absorb more. At the wellhead, with a limited quantity of glycol available, the "wetted" glycol is processed to remove the extraneous materials, and the regenerated "clean" glycol is recirculated for reuse. Water vapor and other volatile materials can be taken out of the "wetted" glycol by heating in a reboiler, as known in the art. Glycol can be heated to about 400° F./204° C. at STP before thermal decomposition, and therefore can be heated well above the boiling point of pure water at 212° F./100° C. and the boiling points of various water solutions. But removal of water by boiling or otherwise distilling or evaporating the water does not remove the formerly dissolved chloride salts, and the chloride salts cannot be left to remain and build up in the recirculated glycol because a buildup of undissolved salt will foul and impair the function of both the salt elimination subsystem and the overall natural-gas dehydration system.

The chloride salts are soluble in glycol at lower temperatures, but become less soluble and completely insoluble in glycol at higher temperatures. The solubility of sodium chloride (NaCl) in triethylene glycol (TEG) at standard pressure is 36 g at 40° C., 20 g at 100° C., 5 g at 160° C., and 0 g at 180° C. Therefore, when glycol is heated in a reboiler to the normal operating temperature of 395° F./201° C. sufficient to drive out water and other extraneous materials, the glycol is too hot to take the chloride salts into solution, and the salts will crystallize, precipitate, and form deposits on the heating elements such as the firetube of the reboiler. The salt deposits form a thermal insulator which reduces the efficiency of the reboiler. Increasing the operating temperature of the reboiler to overcome the insulating salt introduces risks of stressing the equipment or thermally degrading the glycol. If the chloride salts are not removed from the "wetted" glycol by a desalting process, then the reboiler will have to be shut down, cooled, emptied, and cleaned periodically to remove the deposited salt, causing interruption to production and requiring additional equipment and personnel time spent at the wellhead.

In the prior art, glycol might be desalted by electrodialysis, distillation or precipitation under a vacuum, membrane separation, strong acid plus strong base ion exchange, or a series of evaporation steps. These prior-art methods have defects such as being batch or non-continuous processes requiring either removing "dirty" glycol for separate off-line regeneration, or stopping the overall natural-gas dehydration process while batch processes are running, or while equipment is being back-flushed or otherwise re-set. Complex processes and complex equipment can be hard to maintain with the resources available at the typical wellhead, leading to the possibility of significant downtime for an entire operation. The prior-art systems and methods can be too complex, too large, too demanding of energy input and operator time and attention, and too expensive to be efficiently practiced at or close to the wellhead in remote locations.

What is needed is a system and method for removal of chloride salt from glycol which can be run in a substantially continuous process, close to the wellhead, requiring minimal resources and maintenance.

U.S. Pat. No. 5,817,889 for a "Process for the Purification of a Glycol Solution," issued on Oct. 6, 1998 to assignee Elf Aquitaine Production, provides for a process where an amount of water is added to a glycol solution to be purified to enable segregation of the resulting mixture into a hydrocarbon phase and a glycol phase. The hydrocarbon phase is separated from the glycol phase and said glycol phase is desalted, e.g., by electrodialysis, to give a desalted and substantially hydrocarbon-free glycol solution which is then concentrated by steam stripping. The method is useful for purifying waste glycol solutions resulting from oil or gas production effluent processing using glycols, and in particular from a gas hydrate inhibition treatment or natural gas dehydration.

U.S. Pat. No. 7,232,505 for a "Method of Regenerating an Aqueous Glycol Solution Containing Salts," issued on Jun. 19, 2007 to assignees Institut Francais du Petrole et al., provides for a method of regenerating a glycol solution containing water, hydrocarbons, and salts. The glycol solution is expanded in drum, then distilled in column. The concentrated glycol collected at the level of reboiler is placed under vacuum to vaporize the water and to precipitate the salts. The salts are separated from the glycol in separation device. The concentrated glycol freed of the salts is stored in capacity.

U.S. Pat. No. 5,882,486 for "Glycol Refining," issued on Mar. 16, 1999 to inventor John W. Moore, Jr., provides for a process where contaminated glycol is refined by vacuum distillation. Specifically, the evaporator is heated to a temperature below the degradation temperature of the glycol. The vacuum is used to bring the flashpoint down sufficiently so that glycol evaporates or flashes at that temperature. The glycol is condensed and filtered through activated granular carbon. The principal use of refining the glycol is to refine the triethylene glycol used in natural gas dehydration plants. For such purposes, the equipment is mounted upon a trailer to be taken to the plant for cleaning glycol. In such instance, in addition to refining the glycol, a cleaning agent (which contains a degreaser) is added to the refined glycol. The glycol is refined while the natural gas dehydration plant is in normal operation and therefore it is not necessary to stop the natural gas dehydration plant for refining the glycol used therein. In addition, by the addition of the cleaning agent, the dehydrating plant equipment may be cleaned while the plant is in normal operation. Another use for refining glycol is anti-freeze glycol. In such instances, the distillation temperatures will be much less but if the process is performed using the same equipment as natural gas, the absolute vacuum pressure will be about the same as before.

U.S. Pat. No. 7,267,775 for a "Gas Processing Method Using a Filtered Glycol Solution," issued on Sep. 11, 2007 to assignee Institut Francais du Petrole, provides for a method and a plant for processing a gas by means of a glycol solution wherein a feed comprising a gas, a glycol, water, and salts is subjected to a first stage of separating the gas from a liquid effluent and said liquid effluent is subjected to a dehydration stage to recover a dehydrated liquid effluent, characterized in that the salts contained in the liquid effluent, dehydrated or not, are eliminated in a membrane separation stage by means of a driving force generated by mechanical pressure difference on either side of a membrane of pore size ranging between 5 and 100 Angstrom. The invention also relates to the use of the method and of the plant for regeneration of a liquid compound of the glycol family used for hydrate formation prevention when using a natural gas.

U.S. Pat. No. 8,876,954 for a "Natural Gas Dehydration Unit with Continuously Fired Reboiler," issued on Nov. 4, 2014 to assignee Moneyhun Equipment Sales and Service Co., provides for a natural gas dehydration system and method that includes a contactor, a flash tank, and a still interconnected by a desiccant circulation system. A continuously fired reboiler is coupled to the still and the flash tank to burn the flash gas from the flash tank and heat the desiccant.

U.S. Pat. No. 4,518,396 for a "Method of Dehydrating Natural Gas," issued on May 21, 1985 to assignee Gas Conditioning Industries, Inc., provides for a method and associated apparatus by which glycols may be cleaned, particularly those which have been used to dehydrate natural gas. Glycol contaminated with water, hydrocarbons, salts such as sodium chloride, and other impurities is degassed and physically separated from immiscible liquid hydrocarbons prior to passing through a quantity of absorbent material to remove the bulk of any residual hydrocarbons and filter particulates. The glycol is then routed through strong acid cation and strong base anion exchange resins to remove salts. The net product of the deionization is water which may easily be removed in a reboiler, yielding a clean, reusable glycol. Glycol which is not contaminated by petroleum impurity may be cleaned by strong acid cation and strong base anion exchange means alone.

U.S. Pat. No. 6,023,003 for a "Process and System for Recovering Glycol from Glycol/Brine Streams," issued on Feb. 8, 2000 to assignee Reading & Bates Development Co., provides for a process and a system for recovering glycol from glycol and brine mixtures produced from oil or natural gas wells that combines energy efficiency with a capability for handling salt and other solids contained in the mixture. The system comprises three effect evaporator systems in series. Each effect evaporator system comprises an evaporator, a separator vessel, product pumps, and a solids removal system. The process utilizes the system to remove salt and other solids as well as excess water leaving a glycol stream that can be reused as a hydrate inhibitor. The process begins by preheating a glycol/brine stream comprising approximately fifty percent (50%) glycol. The stream is then subjected to three evaporation cycles. The first evaporation cycle comprises introducing the preheated stream into a suppressed boiling point evaporator where the stream is heated under a constant pressure. The stream pressure is then dropped to cause a portion of the water contained in the stream to vaporize or flash. The flashing stream is then introduced into a separator vessel where the water vapor is separated from the remaining liquid stream. The water vapor is removed from the separator and condensed. The remaining liquid glycol/brine stream is then pumped from the separator vessel through a solids removal system where precipitated salts and solids are removed. These steps are repeated two additional times. Each time the remaining liquid stream becomes more concentrated with glycol until the finished product is approximately ninety percent (90%) glycol.

U.S. Pat. No. 6,251,166 for a "Glycol Regeneration System Having a Pressurized Reboiler to Remove BTEX Compounds," issued on Jun. 26, 2001 to assignee Anderson Controls, LC, provides for a glycol regenerating system wherein a pressurized reboiler is introduced to a typical prior art system, the pressurized reboiler being in the glycol stream upstream from the conventional atmospheric reboiler. The pressurized reboiler heats the rich glycol coming from the glycol contactor from about 300° F. to 400° F. and keeps the glycol under pressure from about 10-25 psig in order to first distill and condense VOCs (volatile organic compounds) which constitute non-condensable hydrocarbons and condensable hydrocarbons such as BTEX (Benzene, Toluene, Ethylbenzene, Xylene) compounds, the components being conveniently under pressure for transporting the components to a desired location.

SUMMARY OF THE INVENTION

This invention provides a chloride salt eliminator system and method for removal of chloride salt from glycol circulated through a reboiler in natural gas dehydration, in a continuous process, close to the wellhead.

Hot glycol from the reboiler is pumped into a salt eliminator unit having independently replaceable filter elements which trap chloride salts which are not soluble in hot glycol and pass clean glycol for return to the reboiler.

BRIEF DESCRIPTION OF THE DRAWINGS

Reference is made to the drawing, showing a schematic view of the chloride salt eliminator of the invention in use.

DETAILED DESCRIPTION OF THE INVENTION

The chloride salt eliminator 10 system and method provides for removal of chloride salt from glycol circulated through a reboiler in natural gas dehydration, where a glycol such as triethylene glycol (TEG) is used to absorb water, salts, and other unwanted materials from natural gas, in a process usually performed close to the wellhead so that the cleaned natural gas can be transported by pipeline, and where a reboiler 20 is used to heat the previously used "wetted" glycol to an operating temperature of about 395° F./201° C. sufficient to drive out water and other extraneous materials so that the glycol can be reused for additional cycles of dehydration of natural gas. The heating in the reboiler also precipitates out the chloride salts formerly dissolved in the water, which is not soluble in the glycol at the operating temperature of the reboiler, and which therefore crystalizes and precipitates into deposits which are detrimental to the operation of the reboiler and therefore require elimination.

The chloride salt eliminator 10 provides a high-temperature pump 1, driven by a pump motor 2, and controlled by a pump controller 31. The high-temperature pump 1 draws glycol at operating temperature from the reboiler 20, and pumps the hot glycol to the unit inlet 3 of the salt eliminator unit 4. The salt eliminator unit 4 houses several filter elements 5. Each filter element 5 is made of spun glass and has a stainless steel core. The filter elements 5 are arrayed in a series such that the incoming hot glycol will pass through a first filter element 5 and then a second, and so on in series. The filter elements 5 trap chloride salt crystals while passing the glycol. The first filter element 5 will encounter and trap a larger number of crystals up to a point of saturation, after which the glycol will flow around the saturated filter element 5 and flow onto the next filter element 5, which will trap a larger number of crystals until saturation, with the cycle repeating. The filter elements 5 can be removed and replaced independently, allowing the chloride salt eliminator 10 to keep operating or to be paused only very briefly for filter replacement, therefore providing substantially continuous operation. Saturated filter elements 5 can be safely and appropriately discarded or can be cleaned and regenerated, either on site or off site. The provision of a greater number of filter elements provides for greater efficiency in trapping chloride salts and provides for longer operating time between filter maintenance, up to practical limits of size, weight, and complexity for equipment meant to be used in the field close to the wellhead. The filter elements are each of a size appropriate for handling during installation, removal, transport, and storage close to the wellhead. In a preferred embodiment each filter element 5 has a diameter of about 36", the salt eliminator unit 4 houses 13 filter elements 5, and the salt eliminator unit 4 has about 69" overall height and is made of stainless steel. The salt eliminator unit 4 should be able to withstand the high heat and high pressure of operation, plus an additional large margin to withstand increased heat and pressure to ensure safety and reliable operation of the equipment in the field close to the wellhead. In a preferred embodiment, the design temperature of the salt eliminator unit 4 is 650° F. with a normal operating temperature of 395° F. and maximum operating temperature of 400° F. In a preferred embodiment, the design pressure is 125 psig and the operating pressure is 25 psig.

In a preferred embodiment, the high-temperature pump 1 has a capacity of 15 gpm at a 7 psig discharge pressure, and the pump motor 2 is rated 1 hp, 1800 rpm.

The pump controller 31 controls the operation of the high-temperature pump 1 and monitors and controls the pressure of the flow of hot glycol into the salt eliminator unit 4. If the pump controller 31 senses an increase or decrease, matching set conditions, in back pressure in the salt eliminator unit 4, the pump controller 31 will stop the flow of hot glycol and will initiate an alarm protocol, which can include sounding an alarm and sending an alarm signal which can be sent to other parts of the chloride salt eliminator 10 system or to other parts of the overall gas-dehydration or wellhead-operation system. In an embodiment, the pump controller 31 can also monitor, record, and report the volume of hot glycol processed through the chloride salt eliminator 10 system, providing data useful for scheduling maintenance, inspections, and filter changes for the system, and for calculating volume-based billing if needed.

After passing through the filter elements 5 of the salt eliminator unit 4 the hot glycol, free of the chloride salts which have been trapped by the filter elements 5, passes through the unit outlet 6 and is returned to the reboiler 20 for eventual reuse in the natural gas dehydration process.

In an embodiment having an added bypass feature, hot glycol entering the unit inlet 3 of the salt eliminator unit 4 can be diverted to exit through the bypass outlet 7 and return to the reboiler 20 without passing through the filter elements 5. A bypass valve 8 controlled by a bypass controller 32 regulates the bypassing of hot glycol through the bypass outlet 7. The bypass valve 8 and bypass controller 32 can provide an additional measure of safety for operation of the salt eliminator unit 4 by monitoring for out-of-bounds pressure levels and diverting hot glycol back to the reboiler 20. Additionally, the bypass valve 8 and bypass controller 32 can provide for changing filter elements 5 or performing other work without completely shutting down the flow of glycol. The bypass controller 32 can also monitor, record, and report data regarding its operations.

In an embodiment especially suited for operation at or close to the wellhead, the components of the chloride salt eliminator 10 system are mounted on a skid, pallet, or platform, as indicated by the skid boundary 40, to facilitate storage, transport, placement, and operation.

In a remote-operation embodiment, a remote unit 51 is provided, having a remote-unit communications link 52, capable of communicating with a pump-controller communications link 53 and a bypass-controller communications link 54. The remote unit 51 can be implemented as a purpose-built unit or as a software application program for a general-purpose device such as a tablet computer or a smartphone. The communications links can be radio-frequency links such as proprietary links using appropriate frequencies, general-purpose links such as WIFI or BLUETOOTH, or can be cellular data links, where such service is available at the remote locations of drilling operations. The remote unit 51 provides for constant monitoring and reporting of the real-time operating status of the chloride salt eliminator 10 system, plus storage and reporting of additional data collected by the pump controller 31 and bypass controller 32.

Many other changes and modifications can be made in the system and method of the present invention without departing from the spirit thereof. I therefore pray that my rights to the present invention be limited only by the scope of the appended claims.

I claim:

1. A chloride salt eliminator method comprising:
   (i) providing a chloride salt eliminator system comprising:
      (a) a salt eliminator unit having a unit inlet and a unit outlet;
      (b) a plurality of filter elements arrayed within said salt eliminator unit;
      (c) a pump having a pump motor, adapted to pump glycol from a reboiler, into said unit inlet, through said filter elements, and out of said unit outlet back into the reboiler; and
      (d) a pump controller adapted to control operation of said pump;
   (ii) transporting said chloride salt eliminator system to wellhead site;
   (iii) installing said chloride salt eliminator system at the wellhead site;
   (iv) connecting said chloride salt eliminator system to the glycol reboiler of the natural gas dehydration equipment at the wellhead site;
   (v) operating said chloride salt eliminator system in a substantially continuous process;

(vi) changing said filter elements, independently, as needed; and
(vii) removing chloride salts from the glycol circulated through the reboiler.

* * * * *